(12) United States Patent
Lutz

(10) Patent No.: US 6,183,472 B1
(45) Date of Patent: Feb. 6, 2001

(54) PEDICLE SCREW AND AN ASSEMBLY AID THEREFOR

(75) Inventor: Christian Lutz, Bovenau (DE)

(73) Assignee: Howmedica GmbH (DE)

( * ) Notice: Under 35 U.S.C. 154(b), the term of this patent shall be extended for 0 days.

(21) Appl. No.: 09/287,894

(22) Filed: Apr. 7, 1999

(30) Foreign Application Priority Data

Apr. 9, 1998 (DE) .......................................... 298 06 563 U

(51) Int. Cl.⁷ .................................................. A61B 17/58
(52) U.S. Cl. .............................. 606/61; 606/73; 606/104
(58) Field of Search ................................ 606/61, 73, 99, 606/104

(56) References Cited

U.S. PATENT DOCUMENTS 5,720,751 * 2/1998 Jackson ................................. 606/104

* cited by examiner

Primary Examiner—Michael Buiz
Assistant Examiner—Julian W Woo
(74) Attorney, Agent, or Firm—Lerner, David, Littenberg, Krumholz & Mentlik, LLP

(57) ABSTRACT

The invention relates to a pedicle screw and an assembly aid therefor, wherein the pedicle screw comprises a threaded shank and a fork-like head formed by two distanced sections and wherein the sections between themselves form a receiver for an elongate rod and on the sides facing one another there are provided threaded sections into which a threaded element may be screwed for fastening the rod on the head. The head sections of the pedicle screw on the outside comprise a recess, the assembly aid comprises an elongate sleeve in which a shank is axially but rotationally securely displaceable, wherein on the front end of the shank, there are attached two parallel arms arranged at a distance, which with a front gripping section engage into the recesses of the head for transmitting a tension force, between the sleeve and the shank there is provided an adjusting mechanism for the axial relative adjustment of the two parts, and the shank comprises an axial passage for the leading through of a relatively thin tool shank from the rear end of the sleeve until beyond the front end of the shank.

16 Claims, 1 Drawing Sheet

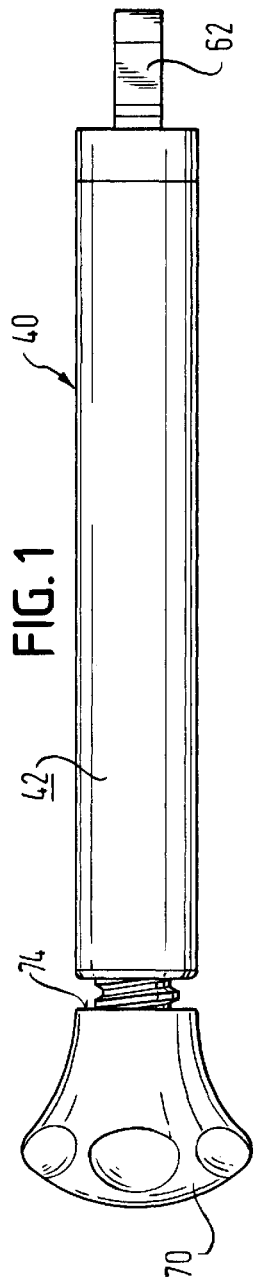
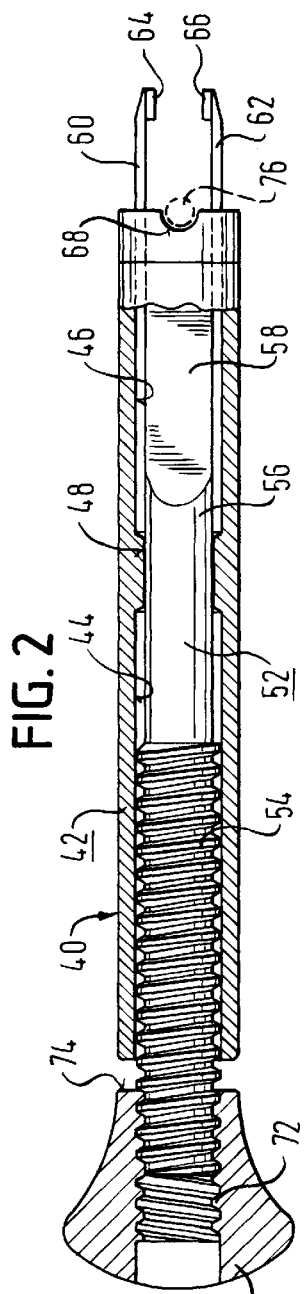
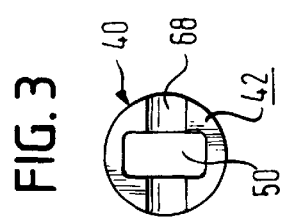
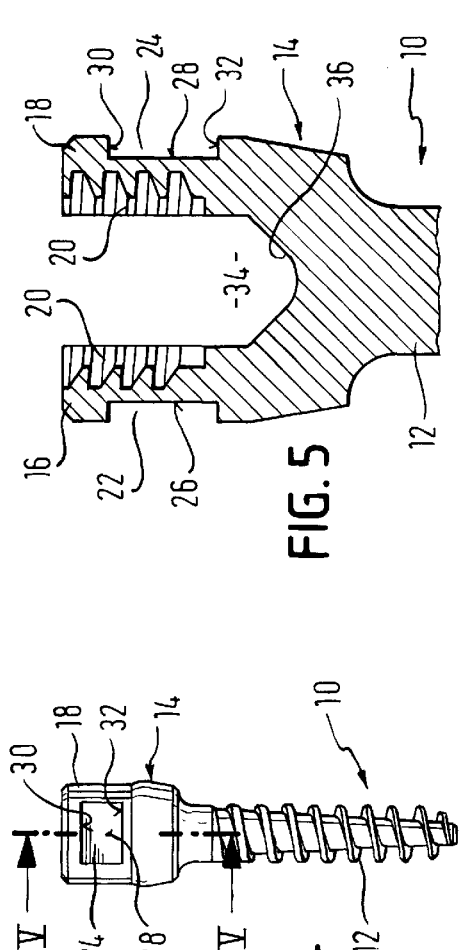
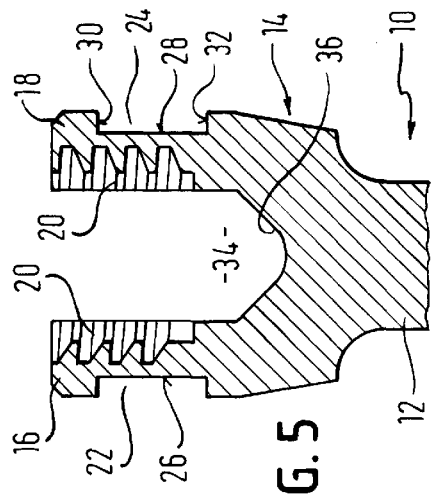

PEDICLE SCREW AND AN ASSEMBLY AID THEREFOR

BACKGROUND OF THE INVENTION

The invention relates to a pedicle screw and an assembly aid therefor.

For the replacement of vertebra of the human spinal column, for the distraction of the spinal column, for the stabilization of the vertebrae and likewise, it is known to apply so-called pedicle screws. They are screwed into the pedicle of the vertebra and comprise a head which is connected to suitable provisions, for example to a stabilizing system, to distraction rods and likewise. It is known to provide pedicle screws with a ring-like head which on the end faces comprises a toothing. It is however also known to form the screw head fork-like so that with this it is in the position to accommodate a distraction rod, a connecting rod or likewise. For fastening the rod in the fork-like head a suitable screw element may be brought into engagement with the head. The screw element may be hat-like and be screwed onto outer threaded sections of the head. It is however also known to allocate an inner thread to the head sections for receiving a set screw or likewise with which the applied rod may be fastened in the head.

It is further known for a more simple handling of the pedicle screw to provide this with a head which is movable relative to the shank, preferably pivotable in all directions. For this purpose the head end of the shank may be formed ball-like, wherein the ball surface cooperates with a spherical bearing surface in the head. In this case it is necessary, after the adjustment of the shank and head to one another has been effected, to retain this angular position. This may for example be effected in that the rod accommodated by the head is pressed against the ball-like head of the shank, by which means the parts are fixed in their position to one another.

In the treatment generally first the pedicle screws are rotated in. Subsequently the insertion of the rod is effected. With this however under certain circumstances considerable forces must be applied in order to move the rod into the fork-like head. The introduction force must be maintained for so long until with the help of the screw element a sliding out of the receiver in the head is no longer possible. For this a considerable amount of dexterity and also a considerable force effort must be carried out on the part or the surgeon.

BRIEF SUMMARY OF THE INVENTION

It is therefore the object of the invention to so form a pedicle screw and so design an assembly aid that the insertion and fixing of rods in the pedicle screw heads are simplified.

An important aspect of the pedicle screw design of the present invention is that recesses are formed on the outer surface of the head. The recess serves for receiving gripping sections which are formed at the end of arms, which for their part are connected to a shank. The shank is slidingly, but rotationally rigidly guided in a sleeve and between the sleeve and the shank there acts an adjusting mechanism, which on actuation displaces the shank relative to the sleeve.

The gripping sections acquire the pedicle screw head from the outer side, so that the head may be moved in the direction of the sleeve with the help of the described adjusting mechanism. The rod has firstly been introduced between the arms, before the pedicle screw has been acquired. If now the screw head is moved in the direction of the sleeve, the sleeve presses the rod automatically between the head sections into the recess.

The shank comprises an axial passage through which a relatively thin shank of a rotary tool may be guided. With the help of the rotary tool, on which already a suitable fastening screw is attached, from now on the set screw may be screwed to the inner threaded sections of the head. By way of this the screw presses the rod against the floor of the receiver. With a sufficiently high tightening force therefore also with a two-part design of a pedicle screw, i.e. with a head mounted pivotably to the screw shank, a fixation in the adjusted angular position may be achieved.

The cooperation of the arms with the outer side of the pedicle screw head may be effected in any suitable way and manner. One formation of the invention for this envisages for the outer contour of the head sections to be convexly rounded and the recess to comprise a floor surface running planarly, parallel to the axis, which in the circumferential direction of the head blends into the outer contour. If the gripping means are for example claw-like attachments on the arms, these may be brought into position laterally to the head and subsequently by way of a movement be laterally aligned to the head. If now relative to the head a tension force is applied to the arms, the claw-like sections acquire the upper wall of the recess and by way of this pull the pedicle screw in the direction of the sleeve of the assembly aid.

The adjusting mechanism may likewise be designed in a known way and manner. Particularly advantageous is an embodiment of the type such that the shank at the rear end comprises an outer thread onto which a handle comprising an inner threaded bore can be screwed, bearing onto the rear end of the sleeve.

In order to obtain a guiding of the rod or wire into the receiver of the pedicle screw head, according to one formation of the invention it is provided for the front end of the sleeve to comprise a diametrical recess which is adapted to the circumferential contour of the rod.

BRIEF DESCRIPTION OF THE DRAWINGS

One embodiment example of the invention is hereinafter described in more detail by way of drawings.

FIG. 1 shows a lateral view of an assembly aid according to the invention.

FIG. 2 shows a section through the assembly aid according to FIG. 1.

FIG. 3 shows the end view of the sleeve of the assembly aid according to FIG. 2.

FIG. 4 shows in a lateral view a pedicle screw for an assembly aid according to the FIGS. 1 to 3.

FIG. 5 shows a section through the head of the pedicle screw according to FIG. 4, along the line 5–5.

DETAILED DESCRIPTION OF THE INVENTION

In the FIGS. 4 and 5 there is indicated a pedicle screw 10. It comprises a threaded shank 12 as well as a head 14. The head 14 is fork-shaped consisting of the sections 16, 18 which on the outside comprise an approximate convex contour. On the inner side threaded sections 20 are provided for receiving a non-shown fastening screw in the form of a set screw or likewise. As can be recognized, a type of saw-tooth thread is provided with the threaded sections 20. This is not gone into in any detail.

On the outer side of the head sections 16, 18 there is formed a recess 22 and 24 respectively. As can be deduced on looking together at FIGS. 4 and 5, the recesses 22, 24 comprise planar floors 26 and 28 respectively which in the circumferential direction blend into the outer contour of the head sections 16, 18. By way of this at the lower and upper end of the recesses 22, 24 there is each formed a shoulder 30 and 32 respectively.

The head sections 16, 18 form a receiver 34 for a non-shown rod, wherein the floor 36 of the receiver 34 is rounded. The rod applied into the receiver 34 may be held or fixed in the receiver with the help of the non-shown fastening screw.

In the FIGS. 1 to 3 there is represented an assembly aid 40. It contains an elongate sleeve 42, which in the inside comprises cylindrical sections 44 and 46 which are separated by a narrow section 48. On the right or front end of the sleeve this is provided with an oval passage 50. The sleeve accommodates a shank 52 which in the left region comprises an outer threaded section 54, in the middle a cylindrical section 56 somewhat smaller in diameter and to the right of this a section 58 oval in cross section, which is formed approximately complementarily to the passage 50 according to FIG. 3. Thus the threaded section 54 is guided approximately through the cylindrical section of the sleeve 44 and the cylindrical section 56 through the inner cylinder section 48 of the sleeve. The oval section 58 of the shank 52 ensures the rotational securement of the shank 52 in the sleeve 46.

At the right end in FIG. 2 on the shank section there are attached two parallel arms 60, 62 which at the free end comprise claw sections 64 and 66 respectively. The sleeve has a diametric semicircular-shaped recess 68 whose axis runs perpendicular to the plane of the arms 60, 62.

The outer threaded section 54 extends to the left beyond the sleeve 42. Onto this threaded section is screwed a knob 70. For this purpose this has an inner threaded section 72. If the knob 70 is screwed onto the outer threaded section 54 with its end surface 74 it abuts the allocated end surface of the sleeve 42 and on further rotation it pulls the shank 52 to the left, by which means the arms 60, 62 move into the sleeve. If the claw-like gripping sections 64, 66 are in engagement with the recesses 22, 24, they pull the accommodated pedicle screw in the direction of the sleeve 42. If between the arms 60, 62 there is applied a rod, as is indicated dashed at 76 in FIG. 2, the rod 76 is gradually moved into the receiver 34 of the head 14.

The shank 52 is drilled through its whole length, and as a result comprises an axial passage through which a relatively thin shank of a rotary tool may be guided. The shank may accommodate a fastening screw which is likewise not shown, for example by way of an insert connection. The combination of the shank rotary tool and the accommodated fastening screw is guided through the shank 52. The fastening screw may then with the help of the rotary tool be screwed into the thread 20 of the head 14 and by way of this move the rod further into the receiver 34 up to the bearing on the floor of the receiver 34. Subsequently the assembly aid 40 may be removed.

The attachment of a pedicle screw on the arms 60, 62 is effected in a manner such that the attachments 64, 66 are moved laterally to the head 14 at the height of the recesses 22, 24. In the same manner the separation of the assembly aid is effected. The arms 60, 62 may spring somewhat and be slightly pretensioned to one another in order to hold the pedicle screw after accommodating the head. It is also possible to align the assembly aid axially to the pedicle screw 10 and to push the arms onto the head 14. The arms 60, 62 are moved laterally apart until the attachments 64, 66 snap into the recess

What is claimed is:

1. A pedicle screw and an assembly aid therefor, wherein the pedicle screw comprises a threaded shank and a fork-like head formed by two distanced sections and wherein the sections between themselves form a receiver for an elongate rod and on the sides facing one another there are provided threaded sections into which a threaded element may be screwed for fastening the rod on the head, wherein the head sections of the pedicle screw on the outside comprise a recess and the assembly aid comprises an elongate sleeve in which a shank is axially but rotationally securely displaceable, wherein on a front end of the shank there are attached two parallel arms arranged at a distance, which with a front gripping section engage into the recesses of the head for transmitting a tension force, between the sleeve and the shank there is provided an adjusting mechanism for the axial relative adjustment of the two parts, and the shank comprises an axial passage for the leading through of a relatively thin tool shank from a rear end of the sleeve until beyond the front end of the shank.

2. A pedicle screw and an assembly aid according to claim 1, wherein the outer contour of the head sections is convexly rounded and the recess comprises a planarly running floor surface parallel to the axis, which in the circumferential direction of the head blends into the outer contour.

3. A pedicle screw and an assembly aid according to claim 1 or 2, wherein the gripping sections are formed by claw-like attachments of the arms.

4. A pedicle screw and an assembly aid according to claim 1, wherein a shank at the rear end comprises an outer threaded section onto which a handle comprising an inner threaded section can be screwed on, bearing onto the rear end of the sleeve.

5. A pedicle screw and an assembly aid according to claim 1, wherein a front end of the sleeve (42) comprises a diametric recess which is adapted to a circumferential contour of a rod.

6. A pedicle screw and an assembly aid according to claim 4 or 5, wherein the handle is formed knob-like.

7. A pedicle screw assembly system comprising:
    a pedicle screw having a threaded end for insertion into a vertebra and an open, generally U-shaped end opposite said threaded end, each leg of said U-shaped end having an outer surface with a shoulder formed thereon said shoulder spaced from said open end of said screw in a direction towards said threaded end; and
    a gripping tool having two arms for engaging said shoulder on said pedicle screw, said arms each having a gripping element for engaging a surface of said shoulder facing said threaded end of said screw wherein said arms are parallel and extend along a plane and wherein said gripping tool further includes a sleeve having a generally cylindrical bore and a shank slideably received in said bore while being prevented from rotating, said shank having a first drive portion and a second portion on which said arms are integrally mounted.

8. The pedicle screw assembly system as set forth in claim 7 further including a knob having an internal threaded bore for receiving a threaded portion of said shank drive portion.

9. The pedicle screw assembly system as set forth in claim 8 wherein said threaded portion of said shank extends beyond an end of said sleeve so that said internal threaded bore of said knob may be threaded onto said shank portion and moved into contact with said end of said sleeve causing said shank to slide within said sleeve.

10. The pedicle screw assembly system as set forth in claim 7 wherein said sleeve has a semi-circular recess formed at an end thereof adjacent to said second portion of said shank, said recess extending in a plane perpendicular to the plan of said arms.

11. The pedicle screw assembly system as set forth in claim 7 wherein said gripping tool further includes a sleeve having a generally cylindrical bore and a shank slideably received in said bore for movement with respect to said sleeve, said shank drive portion having a first threaded portion and a second portion on which said arms are integrally mounted for movement into and out of said sleeve.

12. The pedicle screw assembly system as set forth in claim 11 wherein said generally U-shaped end of said pedicle screw includes an internal thread.

13. The pedicle screw assembly system as set forth in claim 12 wherein said shank includes an axial passage for receiving a rotary tool and a set screw for engaging the internal thread in said U-shaped portion of said pedicle screw.

14. The pedicle screw assembly system as set forth in claim 11 wherein said arms are sprung outwardly on said shank and are forced inwardly by said sleeve when moved into said sleeve.

15. A method of assembling a pedicle screw system comprising the steps of:

providing a pedicle screw having a threaded end for insertion into a vertebra and an open generally U-shaped end opposite said threaded end, each leg of said U-shaped end having an outer surface with a shoulder formed thereon spaced from an open end of said U-shaped end;

providing a gripping tool having a pair of arms with gripping elements formed thereon, said tool having a sleeve and a shank slideably received within said sleeve, said shank having a first threaded portion and a second portion in which said arms are integrally mounted; said arms extending from said sleeve in parallel along a plane;

gripping said shoulder on said pedicle screw with said gripping elements on said arms;

placing a rod on an end of said sleeve adjacent said second portion of said shank in a direction perpendicular to the plane of said arms;

placing a handle with an internal threaded bore on said thread portion of said shank; and turning said handle in a direction to pull said shank and said arms integral therewith towards said sleeve to move said rod within said U-shaped end of said pedicle screw.

16. The method of assembling said pedicle screw system as set forth in claim 15 wherein said shank has a bore and said U-shaped portion of said pedicle screw has internal threads further including the step of:

inserting a set screw and driving tool into said bore of said shank and threading said set screw into said internal threads of said pedicle screw after said rod has been moved into the U-shaped end of said screw.

\* \* \* \* \*